United States Patent [19]

Berdahl et al.

[11] Patent Number: 4,933,469

[45] Date of Patent: Jun. 12, 1990

[54] METHOD FOR PREPARING OXYBISPHTHALIMIDES

[75] Inventors: Donald R. Berdahl, Scotia; Pamela A. Matsch, Schenectady; Susan A. Nye, Feura Bush, all of N.Y.

[73] Assignee: General Electric Company, Schenectady, N.Y.

[21] Appl. No.: 285,165

[22] Filed: Dec. 16, 1988

[51] Int. Cl.$^5$ .......................................... C07D 209/48
[52] U.S. Cl. .................................... 548/476; 548/461
[58] Field of Search ................................ 548/476, 461

[56] References Cited

U.S. PATENT DOCUMENTS

| | | | |
|---|---|---|---|
| 4,273,712 | 6/1981 | Williams, III | 548/461 |
| 4,605,745 | 8/1986 | Brunelle et al. | 548/476 |
| 4,780,544 | 10/1988 | Berdahl | 548/476 |

*Primary Examiner*—Anton H. Sutto
*Assistant Examiner*—Deborah D. Carr
*Attorney, Agent, or Firm*—William H. Pittman; James C. Davis, Jr.

[57] ABSTRACT

A method is provided for preparing oxybisphthalimides by heating a nitrophthalimide compound in the presence of an alkali metal carboxylate, a phase transfer catalyst and a nonpolar organic solvent.

12 Claims, No Drawings

METHOD FOR PREPARING OXYBISPHTHALIMIDES

BACKGROUND OF THE INVENTION

Oxybisphthalimides, for example, 4,4'-oxybis-(N-methylphthalimide), are readily converted by hydrolysis to oxydiphthalic anhydrides, in particular 4,4'-oxydiphthalic anhydride, which is a well known monomer useful in the synthesis of polyimides having good thermal and solvent resistance properties.

The preparation of 4,4'-oxybis-(N-methylphthalimide) (OBI) by heating a solution of 4-nitro-N-methylphthalimide (NPI) with potassium fluoride, potassium or sodium nitrite in a dipolar aprotic solvent, e.g., DMF, Me$_2$SO or NMP and the like, at elevated temperatures has been reported by Markezich, et al., "Reactions of Fluoride and Nitrite Ions with 4-nitrophthalimides", Journal of Organic Chemistry 42, 3481 (1977). OBI has also been synthesized by refluxing NPI with potassium acetate in DMF. The preparation of OBI BY HEATING NPI in a dipolar aprotic solvent in the presence of alkali metal carboxylates has also been reported in U.S. Pat. No. 4,780,544.

The use of dipolar aprotic solvents, e.g., DMF, NMP, sulfolane, DMAc and DMSO, in such methods as described above, however, is undesirable in that such solvents are typically expensive, hard to process and difficult to recycle. A need therefore exists for a process of preparing oxybisphthalimides which utilizes less expensive, relatively nonpolar solvents, which are easier to process and recycle.

SUMMARY OF THE INVENTION

In accordance with the present invention, it has now been surprisingly found that a nitrophthalimide compound of the formula,

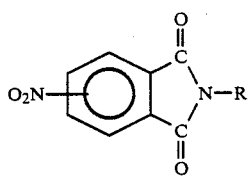

wherein R is C$_{(1-14)}$ monovalent organic radical selected from the class consisting of alkyl radicals, aromatic hydrocarbon radicals, and aromatic hydrocarbon radicals substituted with a member selected from the class consisting of halo, nitro and alkyl radicals, or a mixture thereof, can be converted to the corresponding oxybisphthalimide compound of the formula,

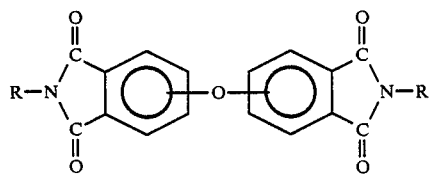

wherein R is as defined above, in good yield by heating the nitrophthalimide compounds in the presence of effective amounts of an alkali metal carboxylate, a phase transfer catalyst, and a nonpolar aprotic organic solvent.

DETAILED DESCRIPTION OF PREFERRED EMBODIMENTS OF THE INVENTION

In accordance with the present invention, a method is provided for preparing oxybisphthalimides which comprises:

(a) heating a nitrophthalimide compound of formula (1) in the presence of effective amounts of an alkali metal carboxylate, a phase transfer catalyst and a nonpolar aprotic organic solvent at a temperature ranging from about 100° C. to about 400° C., then (b) recovering from the resulting mixture of (a) an oxybisphthalimide compound of formula (2).

Representative radicals which are suitable as R in formula (1) include, for example, monovalent C$_{(1-14)}$ alkyl radicals and monovalent C$_{(6-14)}$ aromatic hydrocarbon radicals substituted with monovalent radicals such as halo, nitro and alkyl, preferably which are neutral during reaction. Specific examples of compounds of formula (1) include 4-nitro-N-methyl-phthalimide, 3-nitro-N-methylphthalimide, 4-nitro-N-phenylphthalimide, and 4-nitro-N-butylphthalimide.

Representative examples of oxybisphthalimide compounds of formula (2) prepared by the method of the present invention include 4,4'-oxybis-N-methylphthalimide, 3,3'-oxybis-N-methylphthalimide, 4,4'-oxybis-N-phenylphthalimide and 4,4'-oxybis-N'-butylphthalimide.

Alkyl metal carboxylates which are useful in the practice of the invention include, for example, potassium acetate, potassium benzoate, potassium propionate, sodium acetate, sodium benzoate, cesium acetate, cesium benzoate and the like. Potassium alkyl carboxylate salts and cesium alkyl carboxylate salts are generally preferred. However, depending upon particular reaction conditions and reactants employed, sodium carboxylates become practical alternatives affording high yields of oxybisphthalimide product, and are preferred as such sodium carboxylates are generally cheaper than their respective potassium counterparts. Also contemplated in the practice of this invention are the use of potassium fluoride and potassium nitrite in place of potassium acetate depending upon the particular reaction conditions and end results contemplated.

Phase transfer catalysts suitable for use in the practice of this invention include diorganoaminopyridinium salts of the formula,

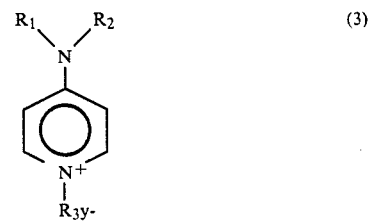

where R$_1$ and R$_2$ are monovalent or divalent organo radicals selected from C$_{(1-13)}$ hydrocarbon radicals and C$_{(13)}$ substituted hydrocarbon radicals and C$_{(1-8)}$ divalent alkylene radicals which can be part of a cyclic structure forming a C$_{(4-12)}$ ring, and where R$_3$ is selected from C$_{(4-18)}$ linear or branched alkyl radicals and y is a counter ion. Such diorganoaminopyridinium salts are particularly preferred as phase transfer catalysts in the practice of the present invention as they have been found to be highly thermally stable.

Representative examples of such preferred phase transfer catalysts are the corresponding chloride, bromide, methane sulfonate and nitrite salts of N-(2-ethylhexyl)-4-dimethylaminopyridine, N-(2-ethylhexyl)-4-(4-methylpiperidinyl) pyridine, N-(2-ethylhexyl)-4-dibutylaminopyridine, N-(2-ethylhexyl)-4-dihexylaminopyridine, 4-dimethylaminopyridine, N-neopentyl-4-(4-methylpiperdinyl) pyridine, N-neopentyl-4-dibutylaminopyridine, N-neopentyl-4-dihexylaminopyridine, N-neopentyl-4-(N,N'-dibutylamino) pyridine, N-octyl-4-dimethylaminopyridine, N-butyl-4-dimethylaminopyridine, and N-dodecyl-4-dimethylaminopyridine.

The preparation of such catalyst compounds is described in detail, for example, in U.S. Pat. No. 4,605,745 which is incorporated by reference herein.

Other simple tetraalkyl ammonium and phosphonium salts such as described, for example, in U.S. Pat. Nos. 4,273,712 and 4,257,953 have also been found to catalyze the reaction in the method of the present invention. Examples of such compounds include, for example, tetraphenylphosphonium bromide, methyltriphenylphosphonium bromide and the like. The use of such compounds is not encouraged, however, as they tend to be unstable and prone to severe decomposition, and oftentimes result in the production of unwanted side products thereby detracting from the oxybisphthalimide product yield.

Nonpolar aprotic organic solvents useful herein preferably include high boiling solvents such as chlorobenzene, dichlorobenzene, trichlorobenzenes, diphenyl ether and diphenyl sulfone, and any other nonpolar organic solvent which does not react with the reactants during the formation of the oxybisphthalimide, for example, xylene, cyclohexanone benzonitrile, and the like.

In the practice of the present invention, the nitrophthalimide compound is heated in the presence of effective amounts of the alkali metal carboxylate, phase transfer catalysts and nonpolar aprotic solvent Experience has shown that an effective amount of the alkali metal carboxylate (or other alternate compounds discussed herein) ranges from about 0.1 to about 5 molar equivalents of nitrophthalimide, preferably from about 0.5 to about 1 equivalents. Further, the phase transfer catalyst as previously defined, can be utilized within the range of from 2.5 to 30 mole percent of catalyst, per mole of nitrophthalimide, and preferably from about 5 to about 10 mole percent.

Experience has also shown that the ensuing reaction can best be run using a solids concentration in the range of between about 5% to about 805 by weight of solids, based on the total weight of solvent employed, and preferably from between about 30% to about 55%.

The reaction is preferably conducted under a nitrogen atmosphere while simultaneously continuously removing water from the reaction mixtures whereby significant increases in reaction rate, product yield and/or purity are observed. Reaction times of from 0.5 to 30 hours are typically employed.

The oxybisphthalimide can be removed from the reaction mixture by a variety of procedures, for example, by allowing the reaction mixture to cool, followed by the recovery of the oxybisphthalimide product by filtration.

In a further aspect of the method of the present invention, experience has shown that the phase transfer catalyst and by-products of the reaction can be recycled directly for further use in the production of oxybisphthalimide in accordance with the practice thereof. For example, in the situation where the reaction mixture is allowed to cool to room temperature to effect separation of the oxybisphthalimide product, the filtrate can be reused as a source of the phase transfer catalyst and the nonpolar organic solvent.

The following detailed examples will serve to more fully illustrate the practice of the present invention. Such examples are intended to be for illustrative purposes only and are not intended to limit the scope of this invention.

EXAMPLE 1

This example demonstrates the use of N-(2-ethylhexyl)-4-dimethylaminopyridinium chloride (EHDMAPCl) as a phase transfer catalyst in the method of the present invention wherein continuous removal of water from the reaction mixture is not carried out. Accordingly, a suitably sized flask equipped with a stirring device, reflux condenser and nitrogen bypass is charged with 4-nitro-N-methylphthalimide (NPI) (10.3 grams, 0.050 mol), EHDMAPCl (1.35 grams, 0.0005 mol), potassium acetate (4.9 grams, 0.050 mol) and reagent grade 1,2-dichlorobenzene (o-DCB) (20 milliliters, reaction 39% solids). The mixture is heated to reflux and the progress of the ensuing reaction monitored by HPLC analysis (reverse-phase, C-18 column, acetonitrile and water). Analysis shows complete disappearance of starting material after approximately six hours, after which the resulting reaction mixture is filtered and the solid washed successively with water and sodium hydroxide (0.15 molar) to yield 4,4'oxybis-N-methyl-phthalimide (OBI) (5.4 grams, 66% yield) having a melting point range of 268-270° C. A similar example without base wash yields OBI in 70% yield.

EXAMILE 2

This example demonstrates the use of EHDMAPCl as a phase transfer catalyst in conjunction with continuous water removal. A suitably sized flask equipped with a stirring device, reflux condenser, nitrogen bypass and Dean-Stark trap equipped to return distillate through 4-40 mesh calcium hydride is charged with NPI (41.2 grams, 0.200 mol) and HPLC grade o-DCB (65 milliliters). The solution is refluxed for one-half hour after which EHDMAPCl (5.4 grams, 0.020 mol), potassium acetate (19.6 grams, 0.200 mol) and additional o-DCB (15 milliliters, reaction 39% solids) are added. The reaction progress is then monitored by HPLC analysis which shows the complete disappearance of starting material after two and one-half hours. After filtering the reaction mixture and wash the solid several times with water and then drying, 24.8 grams, (74% yield) of OBI is obtained having a melting point range of 265-268° C.

EXAMPLE 3

In this example, the preparation of OBI by heating NPI and EHDMAPCl in o-DCB in conjunction with continuous water removal is demonstrated. A flask equipped with a stirring device, reflux condenser, nitrogen bypass and Dean-Stark trap is charged with NPI (41.2 grams, 0.200 mol), EHDMAPCl (5.4 grams, 0.020 mol) and HPLC grade o-DCB (56 milliliters, reaction 39% solids). The solution is heated to reflux and followed by HPLC analysis which indicates the complete disappearance of starting NPI after nine hours. After filtering, washing with water and drying, 17.75 grams

(53) yield) of OBI Is recovered having a melting point range of 265.5–268° C.

EXAMPLE 4

This example demonstrates the synthesis of OBI by heating NPI and 4-dimethylaminopyridine (DMAP) in o-DCB in conjunction with continuous water removal. A flask equipped with a stir bar, reflux condenser, nitrogen bypass and Dean-Stark trap equipped to return distillate through 4-40 mesh calcium hydride is charged with NPI (4.12 grams, 0.020 mol) and HPLC grade o-DCB (12 milliliters). The solution was refluxed for 0.5 hours and while hot, DMAP (0.24 grams, 0.002 mol) is added. A brown gas evolves and after 2 hours, HPLC analysis shows the formation of 5% OBI. This remains relatively unchanged at 5.5 hours. After additional 4-dimethylaminopyridine (2.20 grams, 0.18 mol) is added, heating is continued and the reaction followed by HPLC analysis. After 12 additional hours, NPI is gone and the reaction mixture filtered. The isolated solid is washed several times with water, methanol and then dried giving 2.12 grams of OBI (63% yield) having a melting point range of 250° C.–260° C.

EXAMPLE 5

This example demonstrates the synthesis of OBI by heating NPI, EHDMAPCl, potassium acetate and DMAP in o-DCB while simultaneously continuously removing water. A flask equipped with a stir bar, reflux condenser, nitrogen bypass and Dean-Stark trap equipped to return distillate through 4-40 mesh calcium hydride is charged with NPI (41.2 grams, 0.200 mol) and HPLC grade o-DCB (65 milliliters). After the solution is refluxed for 0.5 hours, DMAP (2.44 grams, 0.02 mol), EHDMAPCl (5.4 grams, 0.020 mol), potassium acetate (19.6 grams, 0.200 mol) and additional HPLC grade o-DCB (15 milliliters, reaction 39% solids) are added. The solution is heated to reflux and the reaction followed by HPLC analysis. Starting NPI is gone after 2 hours and the reaction mixture filtered. The isolated solid is washed several times with water and dried giving 24.14 grams (75% yield) of OBI having melting point 267–270° C.

EXAMPLE 6

This example demonstrates the synthesis of OBI by heating NPI, potassium acetate and DMAP in o-DCB in conjunction with continuous water removal. A flask equipped with a stir bar, reflux condenser, nitrogen bypass and Dean-Stark trap equipped to return distillate through 4-40 mesh calcium hydride is charged with NPI (2.C6 grams, 0.010 mol) and HPLC grade o-DCB (6 milliliters). After the solution is refluxed for 0.5 hours, DMAP (1.22 grams, 0.010 mol), potassium acetate (0.98 grams, 0.010 mol) and additional o-DCB (2.6 milliliters, reaction 27% solids) are added. The solution is heated to reflux and the reaction followed by HPLC analysis which showed 30% OBI in 3.5 hours.

EXAMPLE 7

This example demonstrates the surprising nature of DMAP as a nucleophile in the invention in that another tertiary amine, dimethylaniline, fails to give OBI when heated with NPI in the presence of potassium acetate. A flask equipped with a stir bar, reflux condenser, nitrogen bypass and Dean-Stark trap equipped to return distillate through 4-40 mesh calcium hydride is charged with NPI (2.06 grams, 0.010 mol) and HPLC grade o-DCB (6 milliliters). After the solution is refluxed for 0.5 hours, N,N-dimethylaniline (1.21 grams, 0.010 mol), potassium acetate (0.98 grams, 0.010 mol) and additional o-DCB (2.6 milliliters, reaction 27% solids) are added. The solution is heated to reflux and the reaction followed by HPLC analysis which shows no reaction after 9 hours.

EXAMPLE 8

This example demonstrates the use of tetraphenylphosphonium bromide (TPPBr) as a phase transfer catalyst without continuous water removal. A flask equipped with a stir bar, reflux condenser and nitrogen bypass is charged with NPI (10.3 grams, 0.05 mol), TPPBr (2.09 grams, 0.005 mol), potassium acetate (4.9 grams, 0.05 mol) and HPLC grade o-DCB (11 milliliters, reaction 53.5% solids). HPLC analysis shows the complete disappearance of starting material after 3.5 hours. The reaction mixture is filtered, and the solid washed several times with water and dried 6.60 grams (79% yield) OBI having melting point 252° C.–264° C.

EXAMPLE 9

This example demonstrates the use of TPPBr as a phase transfer catalyst in conjunction with continuous water removal. A flask equipped with a stir bar, reflux condenser, nitrogen bypass and Dean-Stark trap equipped to return distillate through 4-40 mesh calcium hydride was charged with NPI (10.3 grams, 0.05 mol) and HPLC grade o-DCB (9 milliliters). The solution os refluxed for 0.5 hours after which time TPPBr (2.09 grams, 0.005 mol), potassium acetate (4.9 grams, 0.05 mol) and additional o-DCB (3 milliliters, reaction 53.5% solids) are added. HPLC analysis shows the complete disappearance of starting material after 0.5 hours. The reaction mixture is filtered, and the solid washed several times with water and dried giving 6.06 grams (72% yield) OBI having melting point 265° C.–269° C.

EXAMPLE 10

This example demonstrates that methyltriphenylphosphonium bromide (MTPPBr) is relatively ineffective as a phase transfer catalyst in the method of the present invention. A flask equipped with a stir bar, reflux condenser, nitrogen bypass and Dean-Stark trap equipped to return distillate through 4-40 mesh calcium hydride is charged with NPI (10.3 grams, 0.05 mol) and HPLC grade o-DCB (11 milliliters). After the solution is refluxed for 0.5 hours methyltriphenylphosphonium bromide (1.79 grams, 0.005 mol), potassium acetate (4.9 grams, 0.05 mol) and additional o-DCB (2 milliliters, reaction 53.5% solids) are added. The HPLC yield of OBI after 4 hours is only 16%.

EXAMPLE 11

This example demonstrates the need for a phase transfer catalyst in the reaction of NPI with potassium acetate in the method of the present invention. A flask equipped with a stir bar, reflux condenser nitrogen bypass and Dean-Stark trap equipped to return distillate through 40-40 mesh calcium hYdride is charged with NPI (10.3 grams, 0.05 mol) and HPLC grade o-DCB (18 milliliters, reaction 39% solids). After the solution is refluxed for 0.5 hours, potassium acetate (4.9 grams, 0.05 mol) is added. The solution is heated to reflux and the reaction followed by HPLC analysis. Only 5% OBI is observed after 6 hours.

EXAMPLE 12

Example 12 demonstrates that toluene is a less effective solvent for the synthesis of OBI than o-DCB. A flask equipped with a stir bar, reflux condenser, nitrogen bypass and Dean-Stark trap equipped to return distillate through 4-40 mesh calcium hydride is charged with NPI (2.06 grams, 0.010 mol) and toluene (6 milliliters). After the solution is refluxed for 0.5 hours EHDMAPCl (0.27 grams, 0.001 mol) and potassium acetate (0.98 grams, 0.010 mol) are added. The solution is heated to reflux and the reaction followed by HPLC analysis. After 6 hours, chromatographic analysis showed only 11% OBI formed, with 77% starting NPI remaining.

EXAMPLE 13

Example 13 demonstrates the ineffectiveness of tris [2-(2-methoxyethoxy) ethyl] amine (TDA-1) as a phase transfer catalyst in the method of the present invention. A flask equipped with a stir bar, reflux condenser, nitrogen bypass and Dean-Stark trap equipped to return distillate through 4-40 mesh calcium hydride is charged with NPI (10.0 grams, 0.05 mol) and HPLC grade o-DCB (7 milliliters). After the solution is refluxed for 0.5 hours TDA-1 (1.62 grams, 0.005 mol), potassium acetate, (4.9 grams, 0.05 mol) and additional o-DCB (2 milliliters, reaction 39% solids) are added. The solution is heated at reflux and after 5.5 hours, only 9% OBI is observed by HPLC analysis.

EXAMPLE 14

Example 14 demonstrates the synthesis of OBI by heating NPI, EHDMAPCl, and potassium nitrite in o-DCB in conjunction with continuous water removal. A flask equipped with a stir bar, reflux condenser, nitrogen bypass and Dean-Stark trap equipped to return distillate through 4-40 mesh calcium hydride is charged with EHDMAPCl (0.54 grams, 0.002 mol) and HPLC grade o-DCB (11 milliliters). The solution is refluxed for about 0.5 hours, after which time NPI (4.12 grams, 0.020 mol), potassium nitrite (1.70 grams, 0.020 mol) and additional o-DCB (1.75 milliliters, reaction 28% solids) is added. Heating is continued and the reaction followed by HPLC analysis. After 7.5 hours, HPLC analysis showed the reaction mixture to consist of 29% OBI and 66% starting NPI.

EXAMPLE 15

Example 15 demonstrates the synthesis of OBI by heating NPI, EHDMAPCL, and potassium fluoride in o-DCB in conjunction with continuous water removal. A flask equipped with a stir bar, reflux condenser, nitrogen bypass and Dean-Stark trap equipped to return distillate through 4-40 mesh calcium hydride is charged with EHDMAPCl (0.54 grams, 0.002 mol) and HPLC grade o-DCB (11 milliliters). The solution is refluxed for about 0.5 hours, after which time NPI (4.12 grams, 0.020 mol), potassium fluoride (1.16 grams, 0.020 mol) and additional o-DCB (1.75 milliliters, reaction 26% solids) are added. Heating is continued and the reaction followed by HPLC analysis which shows 27% OBI formed after 8 hours and 69% NPI remaining.

EXAMPLE 16

Example 16 demonstrates the synthesis of OBI by heating NPI, EHDMAPCl, and sodium acetate in o-DCB in conjunction with continuous water removal. A flask equipped with a stir bar, reflux condenser, nitrogen bypass and Dean-Stark trap equipped to return distillate through 4-40 mesh calcium hydride is charged with EHDMAPCl (0.54 grams, 0.002 mol) and HPLC grade o-DCB 11 milliliters). The solution is refluxed for 0.5 hours, after which time NPI (4.12 grams, 0.020 mol), sodium acetate (1.64 grams, 0.020 mol) and additional o-DCB (1.75 milliliters, reaction 27% solids) are added. Heating is continued and the reaction followed by HPLC analysis which shows starting NPI completely gone after 9 hours, and the reaction mixture then filtered. The isolated solid is next washed several times with water and dried giving 2.75 grams (82% yield) OBI having a melting point 266° C.-269° C.

EXAMPLE 17

Example 17 demonstrates the use of hexane-1,6-bis-tributylammonium dibromide (C6B) as a phase transfer catalyst in the process of the present invention. A flask equipped with a stir bar, reflux condenser, nitrogen, bypass and Dean-Stark trap equipped to return distillate through 4-40 mesh calcium hydride is charged with NPI (41.6 grams, 0.202 mol) and o-DCB (45 milliliters). The mixture is heated at reflux for 2 hours after which time C6B (12.4 grams, 0.020 mol) and freshly fused potassium acetate (19.8 grams, 0.202 mol) are added. After 3.25 hours, HPLC analysis shows that only 2% NPI remain. The reaction mixture is cooled and filtered and the resulting solid is rinsed well with water and dried yielding 15.3 grams (45% yield) OBI having melting point 230° C.–255° C.

EXAMPLE 18

Example 18 demonstrates the synthesis of OBI by heating NPI, EHDMAPCl and potassium acetate in 1,2,4-trichlorobenzene (TCB) in conjunction with continuous water removal. A flask equipped with mechanical stirrer, reflux condenser, nitrogen bypass, and Dean-Stark trap equipped to return distillate through 4-40 mesh calcium hydride is charged with NPI (38.1 grams, 0.185 mol), EHDMAPCl (5.0 grams, 0.0185 mol), and toluene (80 milliliters) and heated to reflux. After the NPI/EHDMAPCl mixture refluxes for one hour, the toluene is distilled off on a rotary evaporator. TCB (50 milliliters) is added and the Dean-Stark trap filled with activated 4 Å molecular sieves and TCB in place of calcium hydride and toluene. The mixture is heated to reflux at which point freshly fused, powdered potassium acetate (18.1 grams, 0.185 mol) and TCB (15.8 milliliters, total 39% solids) are added. Heating is continued for 45 minutes and then the mixture was cooled and filtered. The resulting solid is washed with water and dried, yielding 24.44 grams (79% yield) OBI of melting point 266° C.–269° C.

EXAMPLE 19

Example 19 demonstrate's the synthesis of OBI by heating NPI, EHDMAPCl and potassium acetate in diphenyl ether in conjunction with continuous water removal. A flask equipped with mechanical stirrer, reflux condenser, nitrogen bypass, and Dean-Stark trap equipped to return distillate through 4-40 mesh calcium hydride is charged with NPI, (38.1 grams, 0.185 mol), EHDMAPCl (5.0 grams, 0.0185 mol), and toluene (80 milliliters) and heated to reflux. After the NPI/EHDMAPCl mixture refluxes for one hour, the toluene is distilled off on a rotary evaporator. Diphenyl ether (70 milliliters) is added and the Dean-Stark trap filled with activated 4 Å molecular sieves and diphenyl ether in place of calcium hydride and toluene. The mixture is heated to reflux at which point freshly fused, powdered potassium acetate (18.1 grams, 0.185 mol) and diphenyl ether (19 milliliters, total 39% solids) are added. Heating is continued for 70 minutes and then the mixture is cooled and filtered. The resulting solid is washed with water and dried, yielding 22.64 grams (73% yield) OBI of melting point 265° C.–267° C.

EXAMPLE 20

Example 20 demonstrates the synthesis of OBI by heating NPI, EHDMAPCl and sodium acetate in 1,2,4-trichlorobenzene (TCB) in conjunction with continuous water removal. A flask equipped with mechanical stirrer, reflux condenser, nitrogen bypass, and Dean-Stark trap equipped to return distillate through 4-40 mesh calcium hydride was charged with NPI, (38.1 grams, 0.185 mol), EHDMAPCl (5.0 grams, 0.0185 mol), and toluene (80 milliliters) and heated to reflux. After the NPI/EHDMAPCl mixture refluxes for one hour, the toluene is distilled off on a rotary evaporator. TCB (50 milliliters) is added and the Dean-Stark trap filled with activated 4 Å molecular sieves and TCB in place of calcium hydride and toluene. The mixture is heated to reflux at which point anhydrous sodium acetate (15.2 grams, 0.185 mol) and TCB (13 milliliters, total 39% solids) are added. Heating is continued for 2 hours and 15 minutes and then the mixture is cooled and filtered. The resulting solid is washed with water and dried, yielding 25.66 grams 83% yield) OBI having melting point 264° C.–265.5° C.

We claim:
1. A method for making oxybisphthalimides which comprises,
   (a) heating a nitrophthalimide compound of the formula,

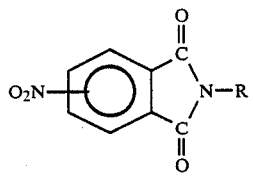
(1)

in the presence of the effective amounts of an alkali metal carboxylate, a phase transfer catalyst, and a nonpolar aprotic organic solvent, at a temperature of from about 100° C. to about 400° C., then
   (b) recovering from the resulting mixture of (a) an oxybisphthalimide compound of the formula,

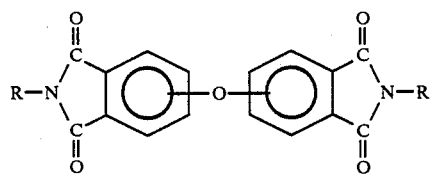
(2)

wherein R is $C_{(1-14)}$ monovalent organic radical selected from the class consisting of alkyl radicals, aromatic hydrocarbon radicals, and aromatic hydrocarbon radicals substituted with a member selected from the class consisting of halo, nitro and alkyl radicals.

2. The method claimed in claim 1 step (a) wherein water is simultaneously continuously removed.

3. The method claimed in claim 2 wherein the nitrophthalimide compound is selected from 4-nitro-N-methylphthalimide, 3-nitro-N-methylphthalimide, 4-nitro-N-phenylphthalimide, and 4-nitro-N-butylphthalimide.

4. The method claimed in claim 2 wherein the nitrophthalimide compound is a mixture of 4-nitro-N-methylphthalimide and 3-nitro-N-methylphthalimide.

5. The method claimed in claim 2 wherein the nitrophthalimide compound is 4-nitro-N-methylphthalimide.

6. The method claimed in claim 2 wherein the alkali metal carboxylate is selected from potassium alkyl carboxylate, sodium alkyl carboxylate and cesium alkyl carboxylate salts.

7. The method claimed in claim 6 wherein the alkali metal carboxylate is selected from potassium acetate, potassium benzoate, potassium propionate, sodium acetate, sodium benzoate, cesium acetate, cesium benzoate and cesium propionate.

8. The method claimed in claim 2 wherein the phase transfer catalyst is a diorganoaminopyridinium salt of the formula,

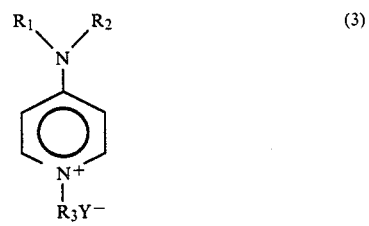
(3)

where $R_1$ and $R_2$ are monovalent or divalent organo radicals selected from $C_{(1-3)}$ hydrocarbon radicals and $C_{(1-3)}$ substituted hydrocarbon radicals and $C_{(1-8)}$ divalent alkylene radicals which can be part of a cyclic structure forming a $C_{(4-12)}$ ring, and where $R_3$ is selected from $C_{(4-18)}$ linear or branched alkyl radicals and Y is a counter ion.

9. The method claimed in claim 8 wherein the phase transfer catalyst is selected from the corresponding chloride, bromide, methane sulfonate and nitrite salts of N-(2-ethylhexyl)-4-dimethylaminopyridine, N-(2-ethylhexyl)-4-(4-methylpiperidinyl) pyridine, N-(2-ethylhexyl)-4-dibutylaminopyridine, N-(2-ethylhexyl)-4-dihexylaminopyridine, 4-dimethylaminopyridine, N-neopentyl-4-(4-methylpiperdinyl) pyridine, N-neopentyl-4-dibutylaminopyridine, N-neopentyl-4-dihexylaminopyridine, N-neopentyl-4-(N,N'-dibutylamino) pyridine, N-octyl-4-dimethylaminopyridine, N-butyl-4-dimethylaminopyridine, and N-dodecyl-4-dimethylaminopyridine.

10. The method claimed in claim 2 wherein the nonpolar aprotic organic solvent is selected from chlorobenzene, dichlorobenzene, trichlorobenzene, diphenyl ether and diphenyl sulfone.

11. The method claimed in claim 2 wherein the alkali metal carboxylate is present in an amount of from about 0.1 to about 5 equivalent of nitrophthalimide, the phase transfer catalyst is present in an amount of from about 2.5 to about 30 mole percent of catalyst per equivalent of nitrophthalimide, and the solids concentration of the resulting mixture in step (a) ranges between 5% to about 80% by weight solids, based on the total weight of solvent present.

12. A composition comprising a nitrophthalimide compound of the formula,

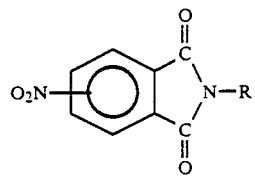

where R is $C_{(1-14)}$ monovalent organic radical selected from the class consisting of alkyl radicals, aromatic hydrocarbon radicals, and aromatic hydrocarbon radicals substituted with a member selected from the class consisting of halo, nitro and alkyl radicals, an alkali metal carboxylate, a phase transfer catalyst and a nonpolar aprotic solvent.

* * * * *